United States Patent [19]

Zinnen et al.

[11] Patent Number: 4,962,273

[45] Date of Patent: Oct. 9, 1990

[54] PURIFICATION OF ALPHA NAPHTHOL-CONTAINING FEEDSTOCK BY ADSORPTION

[75] Inventors: Hermann A. Zinnen, Evanston; Steven P. Johnson, Prospect Heights, both of Ill.

[73] Assignee: UOP, Des Plaines, Ill.

[21] Appl. No.: 264,707

[22] Filed: Oct. 31, 1988

[51] Int. Cl.$^5$ .............................................. C07C 7/12
[52] U.S. Cl. .................................................. 585/831
[58] Field of Search ............... 585/820, 826, 827, 831; 208/310 Z

[56] References Cited

U.S. PATENT DOCUMENTS

| | | | |
|---|---|---|---|
| 2,967,896 | 1/1961 | Fleck et al. | 585/831 X |
| 2,985,589 | 5/1961 | Broughton et al. | 210/34 |
| 3,201,491 | 8/1965 | Stine et al. | 260/676 |
| 3,626,020 | 12/1971 | Neuzil | 260/674 SA |
| 3,663,638 | 5/1972 | Neuzil | 260/674 SA |
| 3,665,046 | 5/1972 | De Rosset | 260/674 SA |
| 3,668,266 | 6/1972 | Chen et al. | 260/674 |
| 3,668,267 | 6/1972 | Hedge | 585/831 |
| 3,686,343 | 8/1972 | Bearden, Jr., et al. | 260/674 SA |
| 3,700,744 | 10/1972 | Berger et al. | 260/668 A |
| 3,840,610 | 10/1974 | Hedge | 585/831 |
| 3,894,109 | 7/1975 | Rosback | 260/674 SA |
| 3,997,620 | 12/1976 | Neuzil | 260/674 SA |
| 4,753,910 | 6/1988 | Han | 502/85 |

OTHER PUBLICATIONS

Chemical Abstracts, vol. 90, 1961 CA95(3):24396W.
Chemical Abstracts, vol. 73, 1970 CA73(16)79141k.
Sorbex a Commercial Proven Route to High Purity Chemicals, J. A. Johnson and H. Zinnen, Mar. 3, 1987.

Primary Examiner—Glenn Caldarola
Attorney, Agent, or Firm—Thomas K. McBride; John F. Spears, Jr.; Jack H. Hall

[57] ABSTRACT

An adsorptive separation process useful in the purification of alpha naphthol-containing feed mixtures, said process comprising the employment of a type X, type Y or a de-aluminated type Y zeolite material and a desorbent material comprising a primary alcohol or an alkyl ester.

31 Claims, 6 Drawing Sheets

PURIFICATION OF ALPHA NAPHTHOL-CONTAINING FEEDSTOCK BY ADSORPTION

BACKGROUND OF THE INVENTION

The field of art to which the claimed invention pertains is adsorptive separation. More specifically, the invention relates to a process for the purification of a feed mixture comprising alpha naphthol and other compounds. In one embodiment, the present invention is a process for obtaining purified alpha naphthol, from its synthesis products, by selectively adsorbing tetralone from a feed mixture comprising alpha naphthol, tetralone and/or tetralin and/or naphthalene. In other embodiments, the alpha naphthol may be selectively adsorbed with the remaining feed components being relatively unadsorbed. In a further embodiment, three or more product streams may be evolved from the process, each containing a distinct relative composition of the feed components. The process employs a particular adsorbent and a particular flow scheme to recover a purified quantity of the alpha naphthol from the feed mixture.

DESCRIPTION OF THE PRIOR ART

Alpha naphthol is an unusually versatile, important, high production volume chemical which finds utility as a raw material in a number of applications. For example, in the field of agricultural chemical products, it is used to produce the products Sevin and Devrinol; in the pharmaceutical industry it finds use in the production of such drugs as Hepalande, Inderol and Alphol; as well as additionally being used in the production of a variety of dyes, rubber and plastic stabilizers and gasoline antioxidants.

One means to the production of alpha naphthol is the conversion of tetralin to alpha naphthol via a two step process. In that process, tetralin is first oxidized to produce tetralone, then the tetralone is aromatized to produce alpha naphthol. Unfortunately, the synthesis process has a potentially detrimental shortcoming related to product purity. Specifically, if either or both steps of the process do not proceed to completion, the ultimate product will contain in addition to the desired product, alpha naphthol, a mixture of other chemical compounds. For example, if the oxidation step is incomplete, thereby allowing tetralin to aromatize, the ultimate product will contain naphthalene, an undesirable impurity. Furthermore, if the aromatization of tetralone is also incomplete, the ultimate product will contain tetralone. Therefore, the synthesis product may be a rather complex mixture of alpha naphthol and/or tetralone and/or tetralin and/or, as stated above, naphthalene. In any such case, one or more further, separation, processing steps will usually be required to achieve the desired alpha naphthol product purity.

To one ordinarily skilled in the art, various means of effecting the desired separation occur. For example, given the large difference in boiling points between the compounds involved, fractional distillation would be an obvious alternative. However, given the relatively high boiling points of alpha naphthol and tetralone, the fractional distillation of such compounds may require operation in a vacuum environment. It is well known that vacuum distillation is an inherently energy intensive process technique, therefore a potentially uneconomic alternative.

On the other hand, adsorptive separation, as generally described in a paper, entitled "Sorbex A Commercially Proven Route to High Purity Chemicals," written by J. A. Johnson and H. A. Zinnen and delivered as part of the Proceedings of the Royal Swedish Academy of Engineering Sciences Symposium, on Mar. 3, 1987, in Stockholm, Sweden, is a possible further alternative technology which was not heretofore known to be an effective alternative separations means in the context of this particular feed mixture with the specificity hereinafter disclosed (i.e., the appropriate combination of apparatus, process technique and sorbents required). Since adsorptive separation would be a desirable, energy efficient, alternative route to the purification of alpha naphthol, it is an object of this invention to describe such appropriate combinations.

It is well known in the separation art that certain crystalline aluminosilicates can be used to separate one hydrocarbon type from another hydrocarbon type. The separation of normal paraffins from branched chain paraffins, for example, can be accomplished by using a type A zeolite which has pore openings from 3 to about 5 Angstroms. Such a separation process is disclosed in U.S. Pat. No. 2,985,589 to Broughton et al, and U.S. Pat. No. 3,201,491 to Stine. These adsorbents allow a separation based on the physical size differences in the molecules by allowing the smaller or normal hydrocarbons to be passed into the cavities within the zeolitic adsorbent while excluding the larger or branched chain molecules.

In addition to being used in processes for separating hydrocarbon types, adsorbents comprising types X or Y zeolite have also been employed in processes to separate individual hydrocarbon isomers. In the processes described, for example, in U.S. Pat. Nos. 3,626,020 to Neuzil, 3,663,638 to Neuzil, 3,665,046 to deRosset, 3,668,266 to Chen et al, 3,686,343 to Bearden, Jr. et al, 3,700,744 to Berger et al, 3,894,109 to Rosback and 3,997,620 to Neuzil, particular zeolitic adsorbents are used to separate para-xylene from other xylene isomers.

With respect to the separation of compounds such as tetralin and naphthalene by adsorption on a sodium form type X zeolite, certain Russian work is available in the prior art. Although the full text apparently appears only in its native language, the relevant ChemAbstracts are available as CA95(3):24396w and CA73(16):79141k. In any event, the disclosures therein made do not appear to teach or suggest the process of the present invention.

More recently, certain innovations have been made in the modification of existing zeolitic materials, specifically, the so-called "de-alumination" technique, whereby some, or essentially all, of the aluminum originally present in the crystalline aluminosilicate structure is removed, resulting in an aluminum-depleted material, finding utility as, inter alia, an adsorbent media. For example, U.S. Pat. No. 4,753,910, issued to Han, describes one such de-alumination technique. Other de-alumination techniques are known to the prior art and are outside the scope of the present invention.

We have found that adsorbents comprising type X, type Y and dealuminated type Y zeolites, at least partially exchanged, at exchangeable cationic sites with appropriate cations, exhibit the ability to selectively adsorb one or more components from a feed mixture comprising tetralone and/or alpha naphthol and/or tetralin and/or naphthalene and possess other desired characteristics thereby achieving improved purification of alpha naphthol from such other feed components by the solid-bed selective adsorption processes. The removal of tetralone and/or such other feed components from such feed mixture yields a purified alpha naphthol product. Of course, if further purification is desired, such may be effected by conventional means such as fractional distillation and/or crystallization so as to result in a desirably pure alpha naphthol product.

SUMMARY OF THE INVENTION

In brief summary the present invention is, in one embodiment, a process for purifying alpha naphthol by separating one or more components from an alpha naphthol-containing feed mixture which process comprises contacting, at adsorptive conditions, said feed mixture with an adsorbent material thereby selectively adsorbing one or more of the components of the feed mixture and thereafter recovering said adsorbed components to an extract stream by contacting said adsorbent material with a desorbent material, at desorptive conditions, and recovering the unadsorbed portion of the feed mixture to a raffinate stream, thereby resulting in a purified alpha naphthol product.

Other embodiments of the present invention encompass details about feed mixtures, adsorbents, desorbent materials, flow schemes and operating conditions all of which are hereinafter disclosed in the following discussion of each of the facets of the present invention.

DESCRIPTION OF THE INVENTION

At the outset, the definitions of various terms used throughout this specification will be useful in making clear the operation, objects and advantages of the process.

A "feed mixture" is a mixture containing one or more extract components and one or more raffinate components to be fed to an adsorbent of the process. The term "feed stream" indicates a stream of feed mixture which passes to an adsorbent used in the process.

An "extract component" is a type of compound or a compound, that is more selectively adsorbed by the adsorbent while a "raffinate component" is a compound or type of compound that is less selectively adsorbed. In this process, depending upon the embodiment, one or more of the feed component(s), is (are) the extract component(s) and the other feed component(s) is (are) a raffinate component. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream" or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated than an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific component, both appearing in the particular stream. For example, the ratio of concentration of the more selectively adsorbed feed mixture components to the concentration of less selectively adsorbed feed mixture components will be highest in the extract stream, next highest in the feed mixture, and lowest in the raffinate stream. Likewise, the ratio of the less selectively adsorbed feed mixture components to the more selectively adsorbed feed mixture components will be highest in the raffinate stream, next highest in the feed mixture, and the lowest in the extract stream. The term "desorbent material" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of desorbent material will be separated at separation conditions to produce an extract product and a raffinate product. The terms "extract product" and "raffinate product" mean products produced by the process containing, respectively, an extract component and a raffinate component in higher concentrations than those found in the respective extract stream and the raffinate stream. The term "selective pore volume" of the adsorbent is defined as the volume of the adsorbent which selectively adsorbs extract components from a feed mixture. The term "non-selective void volume" of an adsorbent is the volume of an adsorbent which does not selectively retain an extract component from a feed mixture. This volume includes the cavities of the adsorbent which contain no adsorptive sites and the interstitial void spaces between adsorbent particles. The selective pore volume and the non-selective void volume are generally expressed in volumetric quantities and are of importance in determining the proper flow rates of fluid required to be passed into the process for efficient operations to take place for a given quantity of adsorbent. When adsorbent "passes" into an operational zone (which zones are used in a preferred embodiment of this process and are hereinafter defined and described) its non-selective void volume together with its selective pore volume carries fluid into that zone. The non-selective void volume is utilized in determining the amount of fluid which should pass into the same zone in a countercurrent direction to the adsorbent to displace the fluid present in the non-selective void volume. If the fluid flow rate passing into a zone is smaller than the non-selective void volume rate of adsorbent material passing into that zone, there is a net entrainment of liquid into the zone by the adsorbent. Since this net entrainment is a fluid present in non-selective void volume of the adsorbent, it in most instances comprises less selectively retained feed mixture components. The selective pore volume of an adsorbent can, in certain instances, adsorb portions of raffinate material from the fluid surrounding the adsorbent since in certain instances there is competition between extract material and raffinate material for adsorptive sites within the selective pore volume. If a large quantity of raffinate material with respect to extract material surrounds the adsorbent, raffinate material can be competitive enough to be adsorbed by the adsorbent.

Feed mixtures which can be utilized in the process of this invention will comprise alpha naphthol, tetralone, tetralin and naphthalene; alpha naphthol, tetralone and tetralin; alpha naphthol and tetralone; alpha naphthol and naphthalene; or alpha naphthol and tetralin, or combinations thereof. As aforesaid, the most likely separation for employment of the present invention, however, is the separation of alpha naphthol from the synthesis products of the two-step oxidation/aromatization reaction of tetralin to alpha naphthol.

To purify alpha naphthol from a feed mixture comprising alpha naphthol, the feed mixture is contacted with the particular adsorbent and depending upon the adsorbent employed, one or more of the feed component(s) is (are) more selectively adsorbed and retained by the adsorbent while the other feed mixture components are relatively unadsorbed and are removed from the interstitial void spaces between the particles of adsorbent and the surface of the adsorbent. The adsorbent containing the more selectively adsorbed extract component(s) is referred to as a "rich" adsorbent—rich in the more selectively adsorbed feed component(s). The extract material is then recovered from the rich adsorbent by contacting the rich adsorbent with a desorbent material.

The desorbent materials which can be used in this process will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which employ zeolitic adsorbents and which are generally operated continuously at substantially constant pressures and temperatures so as to maintain liquid phase, the desorbent material relied upon must be judiciously selected to satisfy several criteria. First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity to the adsorbent for the extract components with respect to the raffinate component.

Desorbent materials to be used in the process of this invention should additionally be substances which are easily separable from the feed mixture that is passed into the process. After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high.

It is therefore contemplated that any desorbent material used in this process will have a substantially different average boiling point than that of the feed mixture to allow separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 5° C. The boiling range of the desorbent material may be higher or lower than that of the feed mixture.

In the preferred isothermal, isobaric, liquid-phase operation of the process of this invention, it has been found that desorbent materials comprising primary alcohols and alkyl esters (i.e., esters of alkanols) having average boiling points substantially different from that of the feed mixture meet those requirements and are particularly effective. Especially preferred for this process are desorbent materials comprising pentanol, methyl acetate or ethyl acetate. Usually one of these preferred desorbent materials or the other can be employed with a particular feed mixture and adsorbent such that the requirement of substantially different average boiling points is met.

The prior art has recognized that certain characteristics of adsorbents are highly desirable, if not absolutely necessary, to the successful operation of a selective adsorption process. Among such characteristics are: adsorptive capacity for some volume of an extract component per volume of adsorbent; the selective adsorption of an extract component with respect to a raffinate component and the desorbent material; and, sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component, the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity, $\beta$, for one component as compared to another component. Relative selectivity can be expressed not only for one feed component as compared to another but can also be expressed between any feed mixture component and the desorbent material. The selectivity, $\beta$, as used throughout this specification is defined as the ratio of the two components of the adsorbed phase over the ratio of the same two components in the unadsorbed phase at equilibrium conditions.

Relative selectivity is shown as Equation 1 below:

$$\text{Selectivity} = \beta \frac{[\text{vol. percent } C/\text{vol. percent } D]_A}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the $\beta$ becomes less than or greater than 1.0 there is a preferential adsorption by the adsorbent for one component with respect to the other. When comparing the selectivity by the adsorbent of one component C over component D, a $\beta$ larger than 1.0 indicates preferential adsorption of component C within the adsorbent. A $\beta$ less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material or, in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process.

In order to test various adsorbents and desorbent material with a particular feed mixture to measure the adsorbent characteristics of adsorptive capacity and selectivity and exchange rate a dynamic testing apparatus is employed. The apparatus consists of an adsorbent chamber of a known (usually, approximately 70 cc-120 cc) volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber.

A pulse test, performed using this apparatus and the following general procedure, is used to determine selectivities and other data for various adsorbent/desorbent systems. The adsorbent is filled to equilibrium with a particular desorbent by passing the desorbent material through the adsorbent chamber. At a convenient time, a pulse of feed containing known concentrations of a non-adsorbed paraffinic tracer ($n$-$C_{14}$, for instance) and of the particular feed material components all diluted in desorbent, is injected for a duration of several minutes. Desorbent flow is resumed, and the tracer and the aromatic isomers are eluted as in a liquid-solid chromatographic operation. The effluent can be analyzed by on-stream chromatographic equipment and traces of the envelopes of corresponding component peaks developed. Alternately, effluent samples can be collected periodically and later analyzed separately be gas chromatography.

From information derived from the chromatographic traces, adsorbent performance can be rated in terms of capacity index for an extract component, selectivity for one isomer with respect to the other, and the rate of desorption of an extract component by the desorbent. The capacity index may be characterized by the distance between the center of the peak envelope of the selectively adsorbed isomer and the peak envelope of the tracer component of some other known reference point. It is expressed in terms of the volume in cubic centimeters of desorbent pumped during this time interval. Selectivity, $\beta$, for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

Adsorbents to be used in the process of this invention will comprise specific crystalline aluminosilicates and de-aluminated crystalline aluminosilicates. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as "molecular sieves" when the separation which they effect is dependent essentially upon differences between the sizes of the feed molecules as, for instance, when smaller normal paraffin molecules are separated from larger isoparaffin molecules by using a particular molecular sieve. In the process of this invention, however, the term "molecular sieves" although widely used is not strictly suitable since the purification of alpha naphthol is apparently dependent on differences in electrochemical attraction of the extract component(s) relative to the other feed components and the adsorbent rather than on pure physical size differences in the molecules of the feed components.

In hydrated form, the crystalline aluminosilicates generally encompass those zeolites represented by the Formula 1a below:

$$M_{2/n}O:Al_2O_3:wSiO_2:yH_2O \quad \text{Formula 1a}$$

where "m" is a cation which balances the electrovalence of the tetrahedra and is generally referred to as an exchangeable cationic site, "n" represents the valence of the cation, "w" represents the moles of $SiO_2$, and "y" represents the moles of water. The generalized cation "M" may be monovalent, divalent or trivalent cations or mixtures thereof.

The prior art has generally recognized that adsorbents comprising the type X and the type Y zeolites can be used in certain adsorptive separation processes. These zeolites are well known to the art.

The type X structured zeolite in the hydrated or partially hydrated form can be represented in terms of mole oxides as shown in Formula 2 below:

$$(0.9\pm0.2)M_{2/n}O:Al_2O_3:(2.5\pm0.5)SiO_2:yH_2O \quad \text{Formula 2}$$

where "M" represents at least one cation having a valence of not more than 3, "n" represents the valence of "M" and "y" is a value up to about 9 depending upon the identify of "M" and the degree of hydration of the crystal. As noted from Formula 2 the $SiO_2/Al_2O_3$ mole ratio is 2.5±0.5. The cation "M" may be one or more of a number of cations such as the hydrogen cation, the alkali metal cation, or the alkaline earth cations, or other selected cations, and is generally referred to as an exchangeable cationic site. As the type X zeolite is initially prepared, the cation "M" is usually predominantly sodium and the zeolite is therefore referred to as a sodium type X zeolite. Depending upon the purity of the reactants used to make the zeolite, other cations mentioned above may be present, however, as impurities.

The type Y structured zeolite in the hydrated or partially hydrated form can be similarly represented in terms of mole oxides as in Formula 3 below:

$$(0.9\pm0.2)M_{2/n}O:Al_2O_3:wSiO_2:H_2O \quad \text{Formula 3}$$

where "M" is at least one cation having a valence not more than 3, "n" represents the valence of "M", "w" is a value greater than about 3 up to 6, and "y" is a value up to about 9 depending upon the identity of "M" and the degree of hydration of the crystal. The $SiO_2/Al_2O_3$ mole ratio for type Y structured zeolites can thus be from about 3 to about 6. Like the type X structured zeolite, the cation "M" may be one or more of a variety of cations but, as the type Y zeolite is initially prepared, the cation "M" is also usually predominantly sodium. The type Y zeolite containing predominantly sodium cations at the exchangeable cationic sites is therefore referred to as a sodium type Y zeolite.

Furthermore, it is known to the prior art that it is possible and, indeed in some cases, preferable to remove from type Y zeolites a portion of the aluminium therein contained. Such de-aluminated type Y zeolites have utility in an embodiment of the present invention Although zeolite Y can be synthesized with a silica-to-alumina ratio ranging from 3 to about 6 and, in some zeolites, for example ZSM-5, the upper limit of silica-to-alumina ratio is virtually unbounded, it is also, as aforesaid, possible to vary the silica-to-alumina ratio of a naturally-occurring or already-synthesized zeolite by chemical treatment. In particular, in view of the relative instability of aluminum in the crystal lattice of a zeolite, a number of methods have been proposed for removing framework aluminum from a zeolite.

For example, in U.S. Pat. No. 4,503,023 a method is disclosed for replacing framework aluminum in an aluminosilicate zeolite having a silica-to-alumina ratio of at least 3 zeolite with framework silicon by contacting the zeolite with an aqueous solution of fluorosilicate salt having a pH of 3 to 7 and in an amount such as to provide at least 0.075 moles of fluorosilicate salt per 100 grams of the zeolite. Other methods are likewise known to the prior art.

Moreover, cations occupying exchangeable cationic sites in the zeolite may be replaced with other cations by ion exchange methods generally known to those having ordinary skill in the field of crystalline aluminosilicates. Such methods are generally performed by contacting the zeolite or a base material containing the zeolite with an aqueous solution of the soluble salt of the cation or cations desired to be placed upon the zeolite. After the desired degree of exchange takes place the sieves are removed from the aqueous solution, washed and dried to a desired water content. By such methods the sodium cations and any non-sodium cations which might be occupying exchangeable sites as impurities in a sodium type X or sodium type Y zeolite can be partially or essentially completely replaced with other cations.

The term "base material" as used herein shall refer to a material containing an X or a Y zeolite and amorphous material which can be used to make the adsorbents used in our process. The zeolite will typically be present in the base material in amounts ranging from about 75 wt. % to about 98 wt. % of the base material based on volatile free composition. Volatile free compositions are generally determined after the base material has been calcined at 900° C. in order to drive off all volatile matter. The remainder of the base material will generally be amorphous material such as silica, alumina or silica alumina mixtures or compounds, such as clays, which material is present in intimate mixture with the small particles of the zeolite material. This amorphous material may be an adjunct of the manufacturing process for X or Y zeolite (for example, intentionally incomplete purification of either zeolite during its manufacture) or it may be added to relatively pure X or Y zeolite but in either case its usual purpose is as a binder to aid in forming or agglomerating the hard crystalline particles of the zeolite. Normally the base material will be in the form of particles such as extrudates, aggregates, tablets, macrospheres or granules having a desired particle size range. The adsorbent used in this process will preferably have a particle size range of about 16–60 mesh (Standard U.S. Mesh). Examples of suitable base materials which can be used to make the adsorbents employed in our process are Type 13X and LZY-56 both of which are available from Union Carbide Corporation. The Type 13X material of course contains X zeolite while the LZY-56 material contains Y zeolite.

The de-aluminated type Y zeolite material employed in an embodiment of the present invention is available commercially from The Toyo Soda Company of Japan under the designation US-Y-9.

It has been found that an adsorbent comprising a type X or type Y and de-aluminated type Y zeolite containing, at exchangeable cationic sites, sodium; sodium or calcium; and sodium and/or hydrogen cations, respectively, satisfies the selectivity requirements and other adsorbent requirements previously discussed and are therefore preferred for use in this process. Adsorbents for this process may be prepared by at least partially or essentially completely ion exchanging sodium forms of the appropriate type base material, in a particle size range of from about 20 to about 40 U.S. Mesh, with the above-mentioned selected cation. Dealuminated Y zeolite such as USY-9 contains little aluminum and hence has little ion exchange capability. Typically the ion exchanges will be done with aqueous solutions of the soluble salts, such as the chlorides, of the respective metal. The term "essentially complete" shall mean that the residual sodium content of the adsorbent after the ion exchange of the base material shall be less than about 2 wt. % $Na_2O$. After ion-exchange and water wash to remove excess ion exchange solution, the adsorbent will be dried to reduce the water content as measured by loss on ignition (LOI) at 900° C. to less than about 10 wt. % and more preferably within a range of from about 1 to about 2 wt. %.

The adsorbent may be employed in the form a dense fixed bed which is alternatively contacted with a feed mixture and a desorbent material in which case the process will be only semicontinuous. In another embodiment a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Separation processes employing countercurrent moving-bed or simulated moving-bed countercurrent flow systems, however, have much greater separation efficiencies than do separation processes employing fixed adsorbent bed systems. With the moving-bed or simulated moving-bed flow systems a feed mixture and a desorbent material are continuously fed to the process and adsorption and desorption are continuously taking place which allows continuous production of an extract output stream and a raffinate output stream. In a preferred embodiment therefore the process will use such flow systems.

In a more preferred embodiment the process will employ a simulated moving-bed countercurrent flow system. The operating principles and sequence of operation of one such simulated moving-bed countercurrent flow system are described in U.S. Pat. No. 2,985,589 incorporated herein by reference. In such a system it is the progressive movement of multiple liquid access points down an adsorbent chamber that simulates the upward movement of an adsorbent contained in the chamber. Only four of the access lines are active at any one time; the feed input stream, desorbent inlet stream, raffinate outlet stream, and extract outlet stream access lines. Coincident with this simulated upward movement of a solid adsorbent is the movement of a liquid occupying the void volume of the packed bed of adsorbent. So that countercurrent contact is maintained, a liquid flow down the adsorbent chamber may be provided by a pump. As an active liquid access point moves through a cycle, that is, from the top of the chamber to the bottom, the chamber circulation pump moves through different zones which required different flow rates. A programmed flow controller may be provided to set and regulate these flow rates.

The active liquid access points effectively divided the adsorbent chamber into separate zones, each of which has a different function. In this embodiment of our process it is generally necessary that three separate operational zones be present in order for the desired operations to take place although in some instances an optional fourth zone may be used.

The adsorption zone, zone 1, is defined as the adsorbent located between a feed inlet stream and raffinate outlet stream. In this zone, a feed mixture contacts an adsorbent, an extract component is adsorbed, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the adsorbent between an extract outlet stream and the feed inlet stream. The basic operations taking place in zone 2 are the displacement from the non-selective void volume of the adsorbent of any raffinate material carried into zone 2 by the shifting of adsorbent into this zone and the desorption of any raffinate material adsorbed within the selective pore volume of the adsorbent or adsorbed on the surfaces of the adsorbent particles. Purification is achieved by passing a portion of extract stream material leaving zone 3 (hereinafter described) into zone 2 at zone 2's upstream boundary, the extract outlet stream, to effect the displacement of raffinate material. The flow of material in zone 2 is in a downstream direction from the extract outlet stream to the feed inlet stream.

Immediately upstream of zone 2 with respect to the fluid flowing in zone 2 is the desorption zone or zone 3. The desorption zone is defined as the adsorbent between a desorbent inlet stream and the extract outlet stream. The function of the desorption zone is to allow a desorbent material which passes into this zone to displace the extract component which was adsorbed upon the adsorbent during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the adsorbent between the raffinate outlet stream and the desorbent inlet stream, if used, is located immediately upstream with respect to the fluid flow to zone 3. Zone 4 would be utilized to conserve the amount of desorbent utilized in the desorption step since a portion of the raffinate stream which is removed from zone 1 can be passed into zone 4 to displace desorbent material present in that zone out of that zone into the desorption zone. Zone 4 will contain enough adsorbent so that raffinate material present in the raffinate stream passing out of zone 1 and into zone 4 can be prevented from passing into zone 3 thereby contaminating the extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of an adsorbent can be accomplished by utilizing a manifold system in which the valves in the manifold are operated in a sequential manner to effect the shifting of the input and output streams thereby allowing a flow of fluid with respect to solid adsorbent in a countercurrent manner. Another mode of operation which can effect the countercurrent flow of solid adsorbent with respect to fluid involves the use of a rotating disc valve in which the input and output streams are connected to the valve and the lines through which feed input, extract output, desorbent input and raffinate output streams pass are advanced in the same direction through the adsorbent bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of an adsorbent than some other operational zone. For instance, in some operations the buffer zone can contain a minor amount of an adsorbent as compared to the adsorbent required for the adsorption and purification zones. It can also be seen that when a very efficient desorbent material is used which can easily desorb an extract component from an adsorbent, it is possible that a relatively small amount of adsorbent will be needed in a desorption zone as compared to the adsorbent needed in the buffer zone or adsorption zone or purification zone. It is not required that an adsorbent be located in a single column which is divided into zones, and the use of multiple chambers or a series of columns is also within the scope of this embodiment.

It is not necessary that all of the input or output streams be simultaneously used, and, in fact, in many instances, some of the streams can be shut off while others effect an input or output of material. One apparatus which can be utilized to effect the process of this invention in a preferred embodiment will contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations function intermittently as a conduit through which material passes into or out of the process.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. Typically the concentration of desorbent material in the extract product and the raffinate product will be less than about 5 vol. % and more preferably less than about 1 vol. %. The separation means will typically be a fractionation column, the design and operation of which is well known to the separation art.

Reference can be made to D. B. Broughton U.S. Pat. No. 2,985,589 and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, for further explanation of the simulated moving bed countercurrent process flow scheme.

Although both liquid and vapor phase operations can be used in many adsorptive separation processes, liquid-phase operation is preferred for this process because of the lower temperature requirements and because of the higher yields of an extract product that can be obtained with liquid-phase operation over those obtained with vapor-phase operation. Adsorption conditions will include a temperature range of from about 20° C. to about 250° C. with about 60° C. to about 200° C. being more preferred and a pressure range of from about atmospheric to about 500 psig (3448 kPa g) with from about atmospheric to about 250 psig (1724 kPa g) being more preferred to insure liquid phase. Desorption conditions will include the same range of temperatures and pressure as used for adsorption conditions.

The size of the units which can utilize the process of this invention can vary anywhere from those of pilot plant scale (see for example U.S. Pat. No. 3,706,812) to those of commercial scale and can range in flow rates from as little as a few cc an hour up to many thousands of gallons per hour.

BRIEF DESCRIPTION OF THE FIGURES

FIGS. 1 through 6 are plots of data obtained during the course of the examples described hereinafter. Specifically, these plots qualitatively describe the capability of the sorbent system employed to resolve the components of the feed material used. To the extent that an object of the present invention is to recover purified alpha naphthol from the feed mixture, it will be evident that those sorbent combinations exemplified by the data showing the clearest resolution of alpha naphthol from the remaining components of the feed mixture are generally most preferred for the practice of the process of the present invention.

The following examples are presented for illustration purposes and more specifically are presented to illustrate the selectivity relationships that make the process of the invention possible. Reference to specific cations, desorbent materials, feed mixtures and operating conditions is not intended to unduly restrict the scope and spirit of the claims attached hereto.

EXAMPLE I

In this experiment a pulse test was performed to evaluate the ability of an adsorbent of the present invention to purify an alpha naphthol-containing feed mixture by adsorptive separation of tetralone. The feed mixture contained tetralone, alpha naphthol and tetralin. The base material contained a Linde sodium type Y structured zeolite bound with an amorphous binder material. The adsorbent was dried to essentially complete dryness before it was utilized in the test.

The testing apparatus was an adsorbent chamber containing approximately 70 cc of the adsorbent and contained with a temperature-controlled means in order to maintain essentially isothermal operations through the column. During the pulse test the column was maintained at a temperature of 100° C. and a pressure of 100 psig (690 kPa g) to maintain liquid-phase operations. The feed mixture employed for this test was 2 cc of a mixture containing 0.5 gram each of alpha naphthol, tetralone, naphthalene, 0.3 gram n-$C_{16}$ which was used as a tracer and 2 cc desorbent material. The desorbent material was methyl acetate. The operations taking place for this test were as follows. The adsorbent bed temperature was maintained at 100° C. and the desorbent material was run continuously at a nominal liquid hourly space velocity (LHSV) of 1.0 which amounted to about 1.17 cc per minute feed rate of desorbent. At some convenient time interval the desorbent was stopped and the feed mixture was run for a 1.71-minute interval at a rate of 1.17 cc per minute. The desorbent stream was then resumed at 1 LHSV and continued to pass into the adsorbent column until all of the feed mixture had been eluted from the column as determined by chromatographic analysis of the effluent material leaving the adsorption column. The attached FIG. 1 comprises a plot of the chromatographic analyses for the feed components and tracer eluted from the column.

Figure 1:
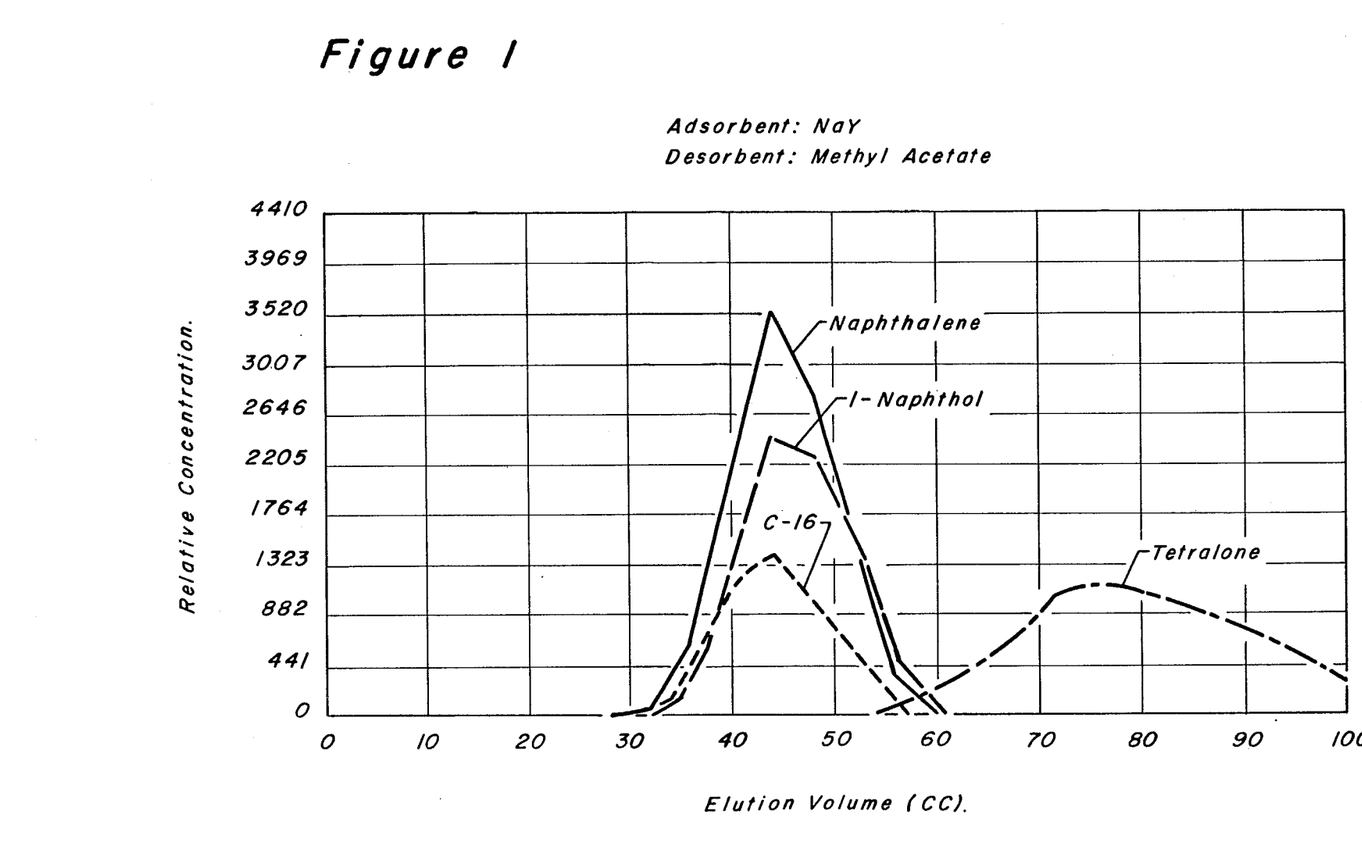

The curves in FIG. 1 show that a sodium type Y zeolite and a methyl ester desorbent is capable of selectively adsorbing tetralone from the feed material, thereby demonstrating the capability of such system to adsorptively purify the alpha naphthol containing feed material.

EXAMPLE II

A second pulse test was performed in all manners similar to that performed for Example I, except that (1) the adsorbent bed temperature was maintained at 135° C.; (2) the desorbent flow was 1.14 cc/min and (3) the feed mixture contained 0.5 gm tetralin in place of the n-$C_{16}$, with the remaining volume being added desorbent.

Figure 2:
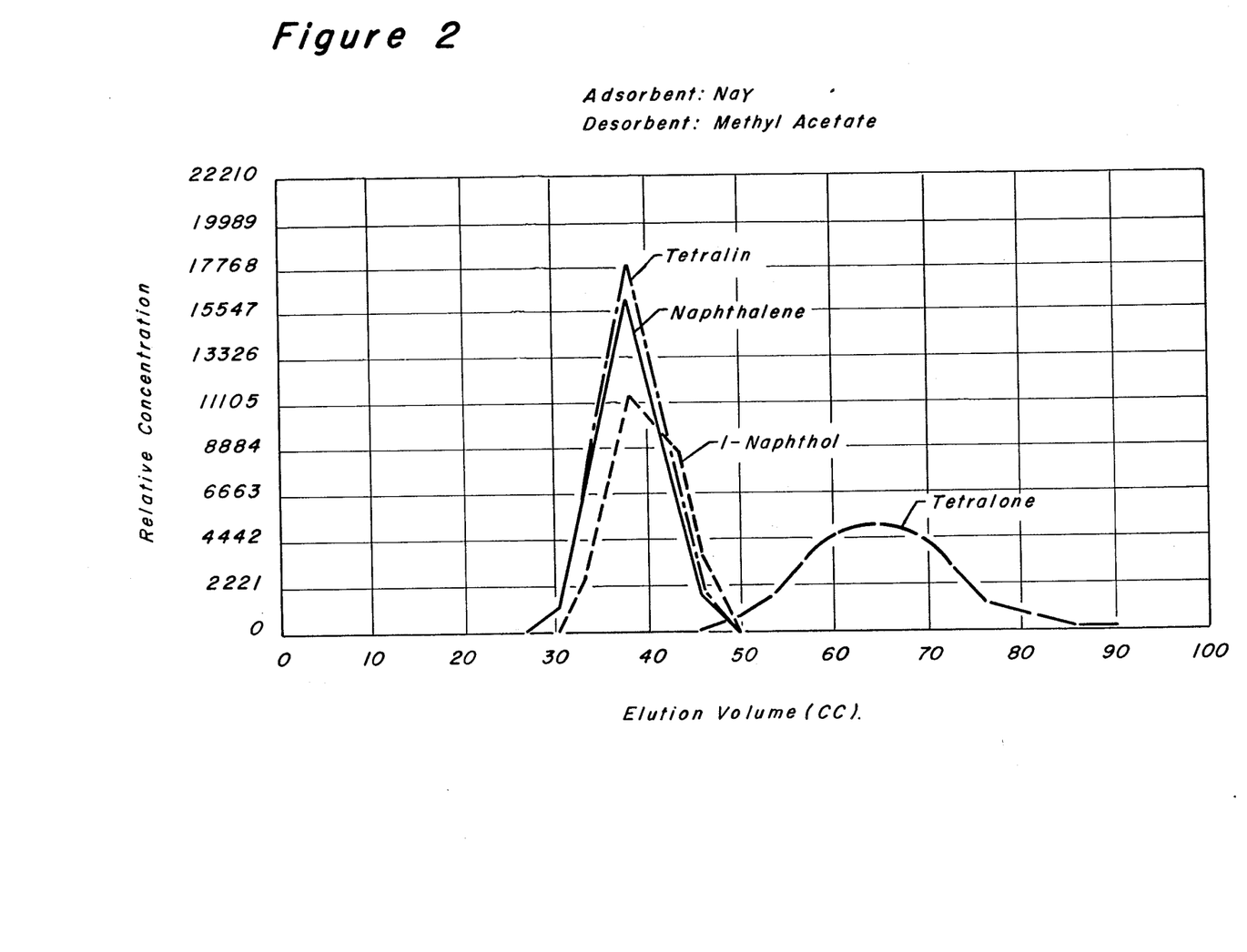

The attached FIG. 2 comprises the chromatographic traces for the feed material eluted from the column.

The curves in FIG. 2 show that compared to the work comprising Example I, at a significantly different temperature, a sodium type Y zeolite and a methyl ester desorbent is capable of selectively adsorbing tetralone from the feed material.

EXAMPLE III

A third pulse test was performed in all manners similar to that performed for Example I, except that (1) The adsorbent was cation exchanged with calcium such that the residual sodium as $Na_2O$ was less than 2.5 wt %, also dried to essentially complete dryness; (2) the adsorbent bed temperature was maintained at 135° C. during the test (3) the feed mixture contained n-$C_{14}$ in place of n-$C_{16}$.

Figure 3:
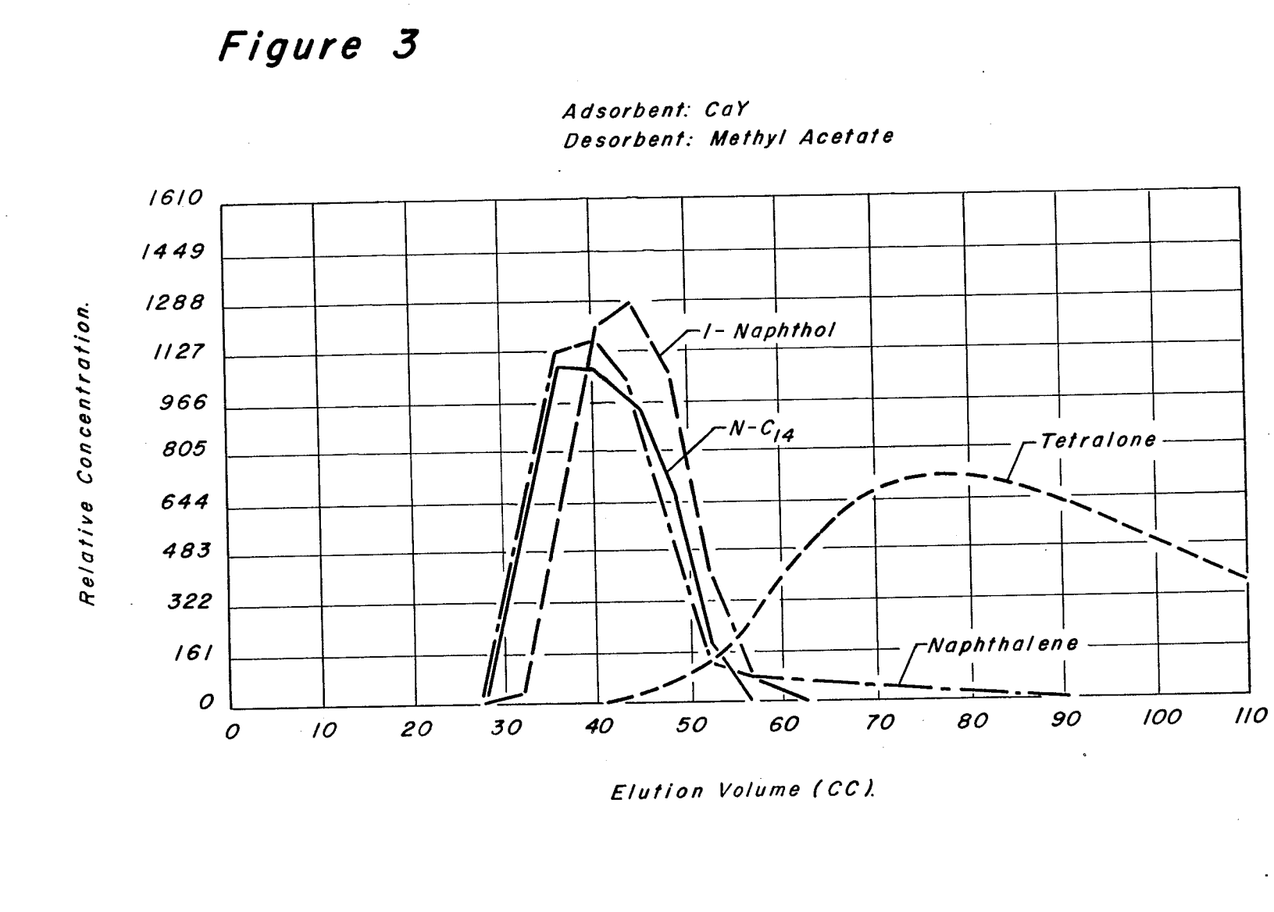

The attached FIG. 3 comprises the chromatographic traces for the feed material eluted from the column.

The curves in FIG. 3 show that a calcium type Y zeolite and a methyl ester desorbent is also capable of selectively adsorbing tetralone from the feed material.

EXAMPLE IV

A fourth pulse test was performed in all manners similar to that performed for Example I, except that (1) the adsorbent was a sodium form type X zeolite again, dried to essentially complete dryness (2) the desorbent used was 100% pentanol and (3) n-$C_{14}$ was used as a tracer in place of n-$C_{16}$.

Figure 4:
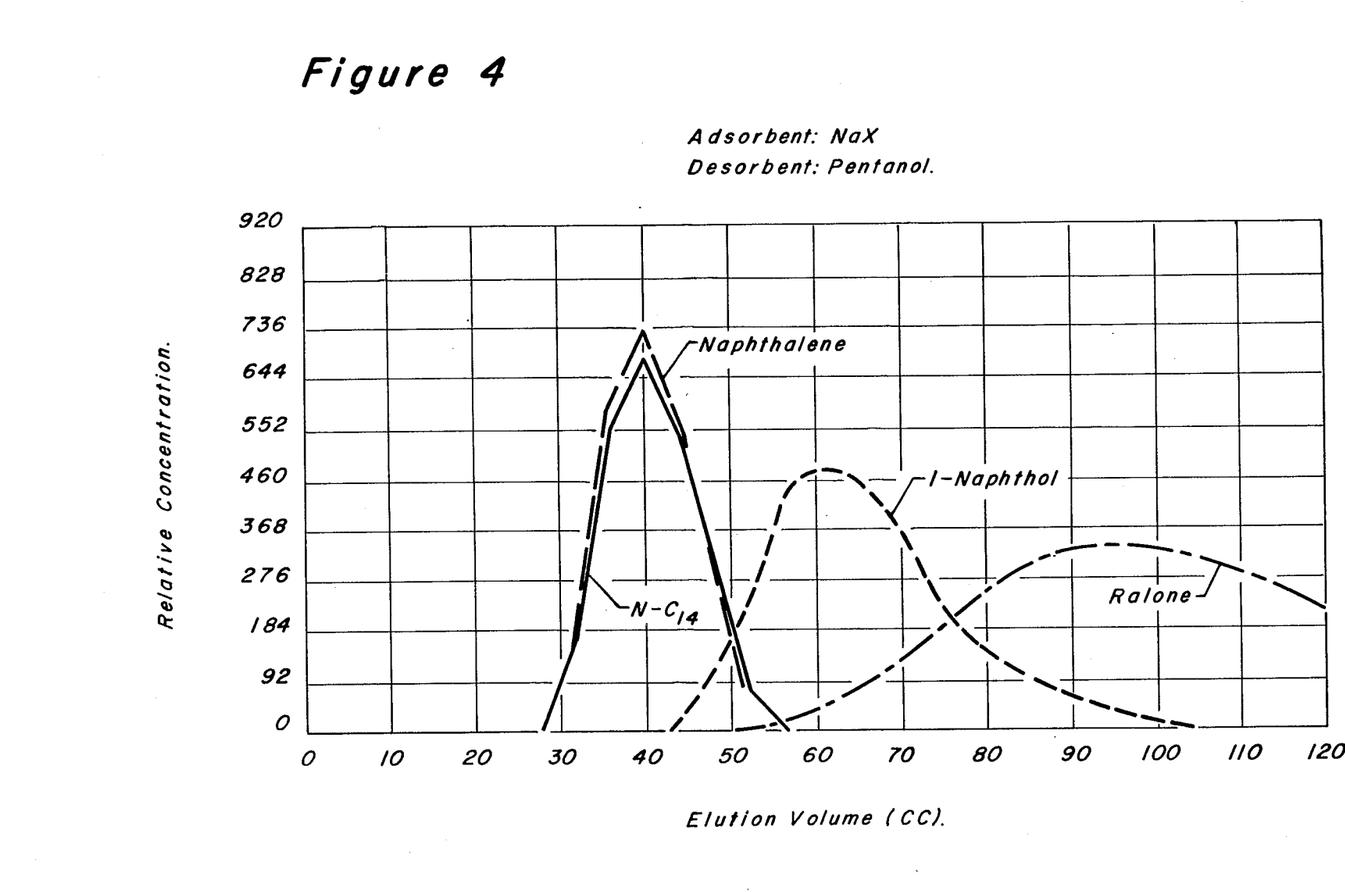

The attached FIG. 4 comprises the chromatographic traces for the feed material eluted from the column.

The curves in FIG. 4 show that at a significantly different temperature, a sodium type X zeolite and a pentanol desorbent is capable of selectively adsorbing tetralone from the feed material. Moreover, it is important to note that the NaX adsorbent is capable of not only selectively adsorbing tetralone over the other components of the feed mixture, but in addition, is capable of resolving each of the three feed components distinctly.

EXAMPLE V

A fifth pulse test was performed in all manners similar to that performed for Example I, except that (1) during the test the adsorbent bed temperature was maintained at 135° C., (2) the feed material was a portion of a commercial alpha naphthol synthesis product to which was added n-$C_{14}$; (3) the desorbent flow rate was 1.08 cc/min.

Figure 5:
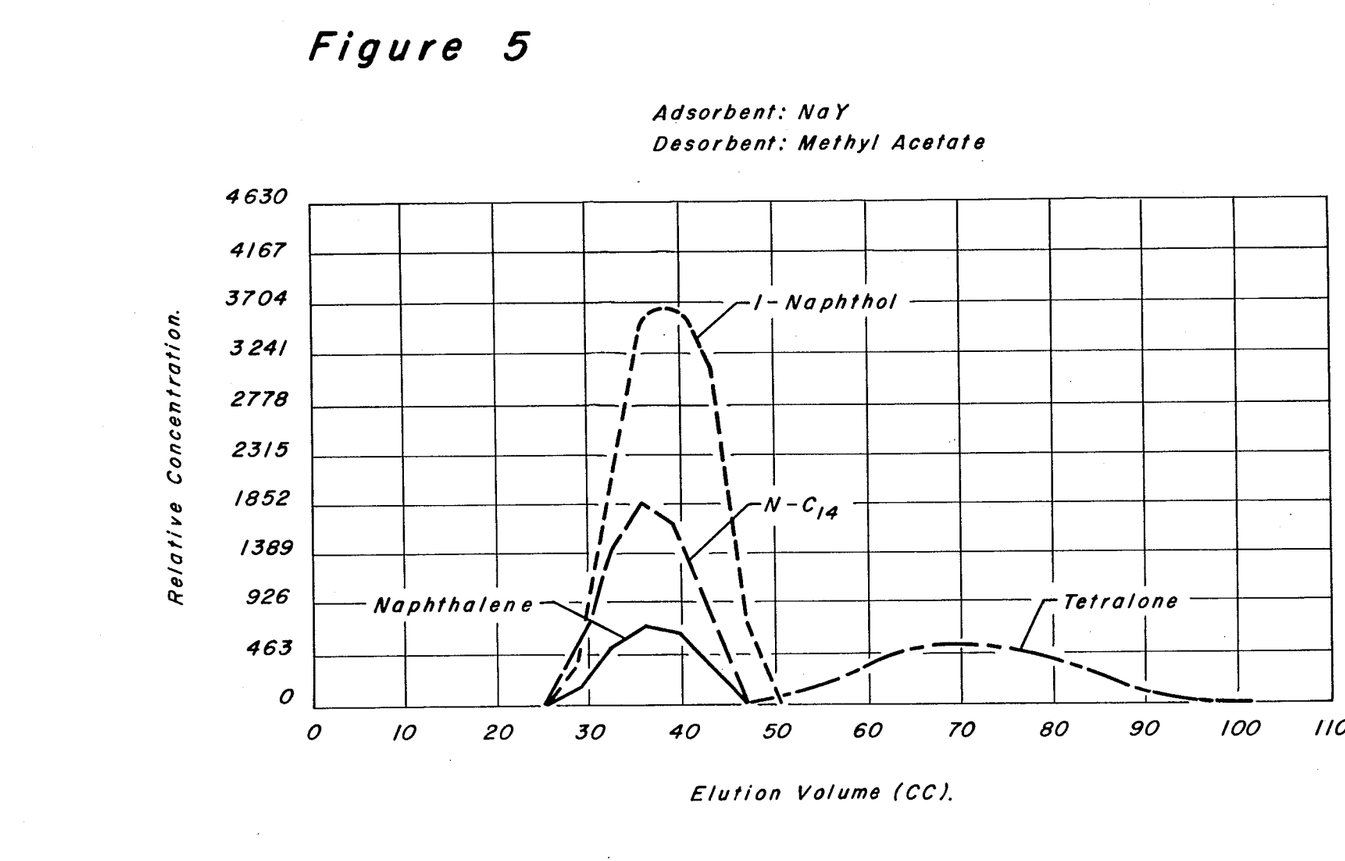

The attached FIG. 5 comprises the chromatographic traces for the feed material eluted from the column.

The curves in FIG. 5 show that a sodium type Y zeolite and a methyl ester desorbent is capable of selectively adsorbing tetralone from a commercial feed material.

EXAMPLE VI

A sixth pulse test was performed in all manners similar to that performed for Example I, except that (1) the adsorbent was a de-aluminated type Y zeolite, manufactured by the The TOYO Soda Company and offered commercially under the designation US-Y 9; (2) the temperature was maintained at 135° C. during the test; (4) the feed material contained n-$C_{14}$ in place of n-$C_{16}$; (5) the desorbent was ethyl acetate; (6) the desorbent flow rate was 1.2 cc/min.

Figure 6:
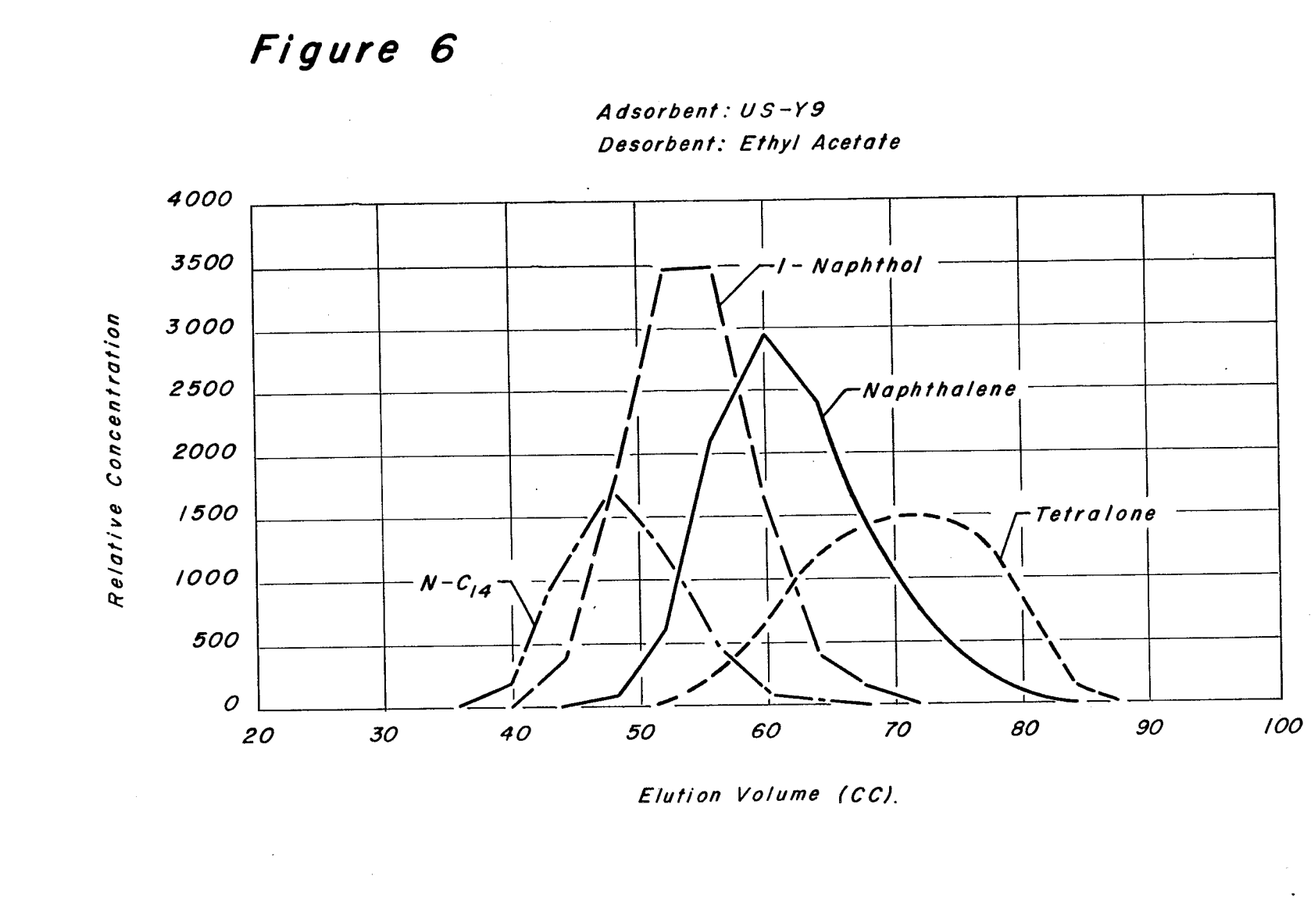

The attached FIG. 6 comprises the chromatographic traces for the feed material eluted from the column.

The curves in FIG. 6 show that a de-aluminated type Y zeolite and an ethyl ester desorbent is capable of selectively adsorbing tetralone from the feed material. Moreover, it is important to note the ability of the de-aluminated type Y adsorbent to resolve each of the feed components distinctly in the following decreasing order of selectivity: tetralone, naphthalene and alpha naphthol. Comparing this to the resolution of the adsorbents used in Examples I (NaY) and IV (NaX), it is apparent that the use of the de-aluminated type Y material yields yet another selectivity option with respect to the resolution of feed components. Adsorbent/desorbent systems capable of resolving three or more feed components distinctly are especially preferred in the operation of the simulated co-current moving bed adsorptive separation process of Gerhold, as described in U.S. Pat. No. 4,402,832 and in the simulated counter current moving bed adsorptive separation process of Broughton, as described in U.S. Pat. No. 2,985,589 described above. In such processes it is possible to simultaneously produce three or more products given an adsorbent/desorbent system such as is demonstrated in Examples IV and VI.

What is claimed is:

1. A process for purifying alpha naphthol by separating one or more components from a feed mixture containing alpha naphthol and one or more compounds selected from the group consisting of naphthalene, tetralin and tetralone which process comprises contacting, at adsorptive conditions, said feed mixture with an adsorbent material thereby selectively adsorbing one or more of the components of the feed mixture and thereafter recovering said adsorbed components to an extract stream by contacting said adsorbent material with a desorbent material, at desorptive conditions, and recovering the unadsorbed portion of the feed mixture including at least a portion of the alpha naphthol to a raffinate stream.

2. The process of claim 1 wherein said adsorbent material is a type X zeolite, which has been at least partially cation exchanged, at exchangeable sites, with sodium cations.

3. The process of claim 1 wherein said adsorbent material is a type Y zeolite, which has been at least partially cation exchanged, at exchangeable sites, with one or more cations selected from the group consisting of sodium and calcium.

4. The process of claim 1 wherein said adsorbent material is a de-aluminated type Y zeolite.

5. The process of claim 1 wherein said feed mixture is derived from the synthesis products of alpha naphthol and contains alpha naphthol.

6. The process of claim 1 wherein the particle size of said adsorbent material is from about 20 to about 40 mesh.

7. The process of claim 1 wherein the desorbent material comprises one or more of the compounds selected from the group consisting of primary alcohols and alkyl esters.

8. The process of claim 7 wherein the primary alcohol is pentanol.

9. The process of claim 7 wherein the alkyl ester comprises one or more compounds of the group consisting of methyl acetate and ethyl acetate.

10. The process of claim 1 wherein said adsorptive and desorptive conditions include a temperature within the range of from about 20° C. to about 250° C. and a pressure within the range of from about atmospheric to about 500 psig (3448 kPa g) so as to maintain liquid phase.

11. A process for purifying alpha naphthol by separating one or more components from an alpha naphthol-containing feed mixture which process comprises contacting, at adsorptive conditions, said feed mixture with an adsorbent material comprising a sodium form type X zeolite, thereby selectively adsorbing one or more of the components of the feed mixture, including alpha naphthol, and thereafter recovering said adsorbed components to an extract stream by contacting said adsorbent material with a desorbent material, at desorptive conditions, and rejecting to a raffinate stream, the remaining components of the feed mixture.

12. The process of claim 11 wherein said adsorbent material is a type X zeolite, which has been at least partially cation exchanged, at exchangeable sites, with sodium cations.

13. The process of claim 11 wherein said adsorbent material is a type Y zeolite, which has been at least partially cation exchanged, at exchangeable sites, with one or more cations selected from the group consisting of sodium and calcium.

14. The process of claim 11 wherein said adsorbent material is a de-aluminated type Y zeolite.

15. The process of claim 11 wherein said feed mixture is derived from the synthesis products of alpha naphthol and contains alpha naphthol and one or more compounds selected from the group consisting of naphthalene, tetralin and tetralone.

16. The process of claim 11 wherein the particle size of said adsorbent material is from about 20 to about 40 mesh.

17. The process of claim 11 wherein the desorbent material comprises one or more of the compounds selected from the group consisting of primary alcohols and alkyl esters.

18. The process of claim 17 wherein the primary alcohol is pentanol.

19. The process of claim 17 wherein the alkyl ester comprises one or more compounds of the group consisting of methyl acetate and ethyl acetate.

20. The process of claim 11 wherein said adsorptive and desorptive conditions include a temperature within the range of from about 20° C. to about 250° C. and a pressure within the range of from about atmospheric to about 500 psig (3448 kPa g) so as to maintain liquid phase.

21. A process for purifying alpha naphthol by separating one or more components from a feed mixture comprising alpha naphthol, which process employs an adsorbent material and which process comprises the steps of:

(a) maintaining net fluid flow through a column of said adsorbent in a single direction, which column contains at least three zones having separate operational functions occurring therein and being serially interconnected with the terminal zones of said column connected to provide a continuous connection of said zones;

(b) maintaining an adsorption zone in said column, said zone defined by the adsorbent material located between a feed input stream at an upstream boundary of said zone and a raffinate output stream at a downstream boundary of said zone;

(c) maintaining a purification zone immediately upstream from said adsorption zone, said purification zone defined by the adsorbent material located between an extract output stream at an upstream boundary of said purification zone and said feed input stream at a downstream boundary of said purification zone;

(d) maintaining a desorption zone immediately upstream from said purification zone, said desorption zone defined by the adsorbent material located between a desorbent input stream at an upstream boundary of said zone and said extract output stream at a downstream boundary of said zone;

(e) passing said feed stream into said adsorption zone at adsorption conditions to effect the selective adsorption of one or more of the components of the feed mixture by said adsorbent material in said adsorption zone and withdrawing a raffinate output stream from said adsorption zone;

(f) passing a desorbent material having a boiling point different than that of the feed mixture to permit separation therefrom by distillation into said desorption zone at desorption conditions to effect the displacement of said adsorbed components of the feed mixture from the adsorbent material in said desorption zone;

(g) withdrawing an extract stream comprising said the extract components and desorbent material from said desorption zone;

(h) periodically advancing through said column of adsorbent material in a downstream direction with respect to fluid flow in said adsorption zone the feed input stream, raffinate output stream, desorbent input stream, and extract output stream to effect the shifting of zones through said adsorbent material and the production of extract output and raffinate output streams.

22. The process of claim 21 wherein said adsorbent material is a type X zeolite, which has been at least partially cation exchanged, at exchangeable sites, with sodium cations.

23. The process of claim 21 wherein said adsorbent material is a type Y zeolite, which has been at least partially cation exchanged, at exchangeable sites, with one or more cations selected from the group consisting of sodium and calcium.

24. The process of claim 21 wherein said adsorbent material is a de-aluminated type Y zeolite.

25. The process of claim 21 wherein said feed mixture is derived from the synthesis products of alpha naphthol and contains alpha naphthol and one or more compounds selected from the group consisting of naphthalene, tetralin and tetralone.

26. The process of claim 21 wherein the particle size of said adsorbent material is from about 20 to about 40 mesh.

27. The process of claim 21 wherein the desorbent material comprises one or more of the compounds selected from the group consisting of primary alcohols and alkyl esters.

28. The process of claim 27 wherein the primary alcohol is pentanol.

29. The process of claim 27 wherein the alkyl ester comprises one or more compounds of the group consisting of methyl acetate and ethyl acetate.

30. The process of claim 21 wherein said adsorptive and desorptive conditions include a temperature within the range of from about 20° C. to about 250° C. and a pressure within the range of from about atmospheric to about 500 psig (3448 kPa g) so as to maintain liquid phase.

31. The process of claim 21 further characterized in that it includes the step of maintaining a buffer zone immediately upstream from said desorption zone, said buffer zone defined as the adsorbent located between the desorbent input stream at a downstream boundary of said buffer zone and a raffinate output stream at an upstream boundary of said buffer zone.

* * * * *